United States Patent
Jensen

(10) Patent No.: US 9,486,393 B2
(45) Date of Patent: Nov. 8, 2016

(54) SINGLE COMPONENT TOOTH ROOT SEALER

(75) Inventor: Steven D Jensen, South Jordan, UT (US)

(73) Assignee: CAO Group, Inc., West Jordan, UT (US)

(*) Notice: Subject to any disclaimer, the term of this patent is extended or adjusted under 35 U.S.C. 154(b) by 0 days.

(21) Appl. No.: 12/972,245

(22) Filed: Dec. 17, 2010

(65) Prior Publication Data
US 2011/0151401 A1    Jun. 23, 2011

Related U.S. Application Data

(60) Provisional application No. 61/284,491, filed on Dec. 18, 2009.

(51) Int. Cl.
*A61K 6/00* (2006.01)

(52) U.S. Cl.
CPC ........... *A61K 6/0067* (2013.01); *A61K 6/0038* (2013.01)

(58) Field of Classification Search
CPC .................................................. A61K 6/0038
USPC ........................................... 433/81, 90, 224
See application file for complete search history.

(56) References Cited

U.S. PATENT DOCUMENTS

| | | | |
|---|---|---|---|
| 3,082,526 A * | 3/1963 | Nitzsche et al. | 433/224 |
| 4,449,938 A * | 5/1984 | Pollak | 523/116 |
| 5,106,301 A * | 4/1992 | Miyahara et al. | 433/214 |
| 5,336,088 A * | 8/1994 | Discko, Jr. | 433/90 |
| 5,457,148 A * | 10/1995 | Lucas | 524/731 |
| 5,534,562 A | 7/1996 | Jensen et al. | |
| 5,548,002 A * | 8/1996 | Schwabe et al. | 523/118 |
| 5,700,148 A | 12/1997 | Fischer et al. | |
| 5,708,052 A | 1/1998 | Fischer et al. | |
| 5,722,833 A | 3/1998 | Fischer et al. | |
| 5,785,527 A | 7/1998 | Jensen et al. | |
| 5,819,921 A * | 10/1998 | Schmid | 206/210 |
| 5,858,332 A | 1/1999 | Jensen et al. | |
| 6,048,202 A | 4/2000 | Jensen et al. | |
| 6,071,528 A | 6/2000 | Jensen | |
| 6,083,489 A | 7/2000 | Fischer et al. | |
| 6,086,370 A | 7/2000 | Jensen et al. | |
| 6,139,820 A | 10/2000 | Fischer et al. | |
| 6,305,936 B1 | 10/2001 | Jensen et al. | |

(Continued)

FOREIGN PATENT DOCUMENTS

EP    0507177 A2 * 10/1992
JP    01186806 A * 7/1989

OTHER PUBLICATIONS

LOCTITE 5248, Technical Data Sheet, Henkel Technologies, (Oct. 2004).*

(Continued)

*Primary Examiner* — Ralph Lewis

(57) ABSTRACT

Example embodiments of the present invention include compositions, materials, and methods that provide a single component tooth root sealer. The single component tooth root sealer can be designed to moisture cure at temperatures found within the human mouth. Examples of the single component tooth root sealer can include silicone compositions, such as condensation silicones of the alkoxy, acetoxy, and oxime type. Further examples of the single component tooth root sealer can include UV/visible light-initiators, antimicrobial agents, and radio-opaque compounds.

4 Claims, 4 Drawing Sheets

(56) References Cited

U.S. PATENT DOCUMENTS

| | | |
|---|---|---|
| 6,306,206 B1 | 10/2001 | Fischer et al. |
| 6,306,370 B1 | 10/2001 | Jensen et al. |
| 6,309,221 B1 | 10/2001 | Jensen |
| 6,309,625 B1 | 10/2001 | Jensen et al. |
| 6,312,671 B1 | 11/2001 | Jensen et al. |
| 6,322,774 B1 | 11/2001 | Jensen et al. |
| 6,354,837 B1 | 3/2002 | Jensen |
| 6,368,576 B1 | 4/2002 | Jensen et al. |
| 6,375,461 B1 | 4/2002 | Jensen et al. |
| 6,387,353 B1 | 5/2002 | Jensen et al. |
| 6,390,817 B1 | 5/2002 | Jensen |
| 6,391,283 B1 | 5/2002 | Jensen et al. |
| 6,409,993 B1 | 6/2002 | Jensen et al. |
| 6,500,004 B2 * | 12/2002 | Jensen et al. ............... 433/228.1 |
| 6,652,282 B2 | 11/2003 | Jensen et al. |
| 6,689,343 B1 | 2/2004 | Allred et al. |
| 6,811,400 B2 | 11/2004 | Jensen et al. |
| RE38,721 E | 4/2005 | Jensen et al. |
| RE38,722 E | 4/2005 | Jensen et al. |
| RE38,823 E | 10/2005 | Jensen et al. |
| 7,320,598 B2 | 1/2008 | Jensen et al. |
| 7,476,049 B2 | 1/2009 | Jensen |
| 7,645,086 B2 | 1/2010 | Zhang et al. |
| 7,704,074 B2 | 4/2010 | Jensen |
| 8,006,696 B2 | 8/2011 | Jensen |
| 8,342,842 B2 | 1/2013 | Jensen |
| 2002/0123024 A1 | 9/2002 | Jensen et al. |
| 2002/0172921 A1 | 11/2002 | Jensen |
| 2002/0177100 A1 | 11/2002 | Jensen et al. |
| 2003/0194682 A1 | 10/2003 | Jensen et al. |
| 2004/0209229 A1 | 10/2004 | Jensen et al. |
| 2006/0078589 A1 | 4/2006 | Jensen et al. |
| 2006/0110705 A1 | 5/2006 | Jensen et al. |
| 2006/0275369 A1 | 12/2006 | Jensen |
| 2006/0280696 A1 | 12/2006 | Jensen |
| 2007/0014862 A1 | 1/2007 | Pameijer et al. |
| 2007/0183987 A1 | 8/2007 | Jensen |
| 2007/0190110 A1 | 8/2007 | Pameijer et al. |
| 2007/0225658 A1 | 9/2007 | Jensen et al. |
| 2007/0265607 A1 | 11/2007 | Cao et al. |
| 2007/0287122 A1 | 12/2007 | Jensen |
| 2008/0071256 A1 | 3/2008 | Cao et al. |
| 2008/0078391 A1 | 4/2008 | Jensen |
| 2008/0103426 A1 | 5/2008 | Jensen |
| 2008/0138146 A1 | 6/2008 | Jensen |
| 2008/0140030 A1 | 6/2008 | Zhang et al. |
| 2008/0160482 A1 | 7/2008 | Jensen |
| 2008/0318190 A1 * | 12/2008 | Suh et al. .................. 433/228.1 |
| 2009/0011385 A1 | 1/2009 | Jensen et al. |
| 2009/0041858 A1 | 2/2009 | Jensen |
| 2009/0087393 A1 | 4/2009 | Jensen et al. |
| 2009/0092947 A1 | 4/2009 | Cao et al. |
| 2009/0155740 A1 | 6/2009 | Jensen et al. |
| 2009/0220917 A1 | 9/2009 | Jensen |
| 2009/0238779 A1 | 9/2009 | Jensen et al. |
| 2010/0109179 A1 | 5/2010 | Jensen |
| 2010/0111591 A1 | 5/2010 | Jensen |
| 2010/0119987 A1 | 5/2010 | Jensen |
| 2010/0145191 A1 | 6/2010 | Jensen |
| 2010/0173267 A1 | 7/2010 | Cao et al. |
| 2010/0210161 A1 | 8/2010 | Jensen |
| 2010/0237281 A1 | 9/2010 | Jensen |
| 2010/0330532 A1 | 12/2010 | Jensen |
| 2011/0068019 A1 | 3/2011 | Jensen et al. |
| 2011/0068020 A1 | 3/2011 | Jensen et al. |
| 2011/0097368 A1 | 4/2011 | Jensen |
| 2011/0111373 A1 | 5/2011 | Jensen et al. |
| 2011/0151401 A1 | 6/2011 | Jensen |
| 2011/0207081 A1 | 8/2011 | Jensen |
| 2011/0212406 A1 | 9/2011 | Jensen |
| 2011/0212409 A1 | 9/2011 | Jensen |
| 2011/0236322 A1 | 9/2011 | Jensen et al. |
| 2011/0271959 A1 | 11/2011 | Jensen |
| 2011/0306005 A1 | 12/2011 | Jensen |
| 2012/0058453 A1 | 3/2012 | Jensen |
| 2012/0090178 A1 | 4/2012 | Jensen |
| 2012/0107767 A1 | 5/2012 | Jensen et al. |

OTHER PUBLICATIONS

LOCTITE, Medical Adhesive Technology, Product Catalogue, copyright Henkel KGaA, 2006.*

* cited by examiner

SINGLE COMPONENT TOOTH ROOT SEALER

CROSS-REFERENCE TO RELATED APPLICATIONS

This application claims the benefit of U.S. Provisional Application No. 61/284,491, filed Dec. 18, 2009, which is incorporated in its entirety herein by reference.

TECHNICAL FIELD OF THE INVENTION

The present disclosure generally relates to the field of dentistry and, more particularly, to the field of dental tooth root sealer compositions and materials as well as methods of sealing tooth roots.

BACKGROUND OF THE INVENTION

Generally, a human tooth includes three main parts: enamel, dentin, and pulp. The composition of the enamel is almost entirely inorganic mineral, while the dentin is a mixture of inorganic mineral and collagen fiber. The enamel and the dentin make up the hard outer structure of the tooth, and therefore, neither the enamel nor the dentin contain nerve endings. On the other hand, the composition of the pulp portion of the tooth includes flesh tissue that is connected to the circulatory and nerve systems of the human body.

As with other tissues in the body, the pulp of the tooth is subject to infections. When the pulp of a tooth becomes infected the pulp swells. The swelling of the pulp causes pain because the pulp is restricted within the fixed orifice of the hard outer surface of the tooth. This pain is commonly called a toothache, and the infection may eventually result in a necrotic tooth.

One conventional method of dealing with a necrotic tooth is administering a root canal treatment. Generally speaking, during a root canal treatment, a dental professional may use a high-speed drill to penetrate the enamel and dentin and expose the pulp chamber within the tooth. The dental professional may then use an endodontic file to sever the pulp at the apex (apical foramen). To reduce the bacterial load within the pulp chamber, the dental professional may use one or more endodontic files to remove as much of the necrotic pulp as possible from the pulp chamber and root canal.

Once the majority of the necrotic pulp is removed, the dental professional may then disinfect any residual infected tissue that remains in the pulp chamber and/or root canal by hydraulically flushing the pulp chamber and root canal with an antimicrobial solution. The canal is then filled with a temporary anti-microbial compound, such as a calcium hydroxide paste or another antimicrobial/antibiotic, after which the pulp chamber is temporarily sealed. The patient is usually prescribed an oral antibiotic and sent home for a couple of weeks to allow complete treatment of the infection.

When the patient returns to the dental professional's office, the dental professional examines the jaw of the patient apically for any signs of any remaining infection. If there are no signs of infection, the dental professional may proceed to remove the temporary sealing material in order to clean and flush out the root canal. At this point of the root canal procedure, the tooth is prepared for the final sealing process of the root ends. Sealing the root ends isolates the pulp chamber from the connective tissue in the jaw, and also seals in any residual contamination or infectious microbes.

The conventional method of filling and sealing the root ends is accomplished using gutta-percha rubber material. Gutta-percha rubber has physical and chemical properties, including inertness, biocompatibility, melting point, ductility and malleability, which have made the gutta-percha rubber a popular choice to fill root canals. In order to fill and seal the root ends, for example, a dental professional may heat the gutta-percha rubber until it melts. The dental profession then can express or inject the gutta-percha into the root end, essentially filling the root canal from the root end upwards towards the pulp chamber (obturation).

One benefit of using gutta-percha rubbers is that gutta-percha rubber is re-treatable in case the tooth requires further work. In particular, if additional work on the tooth is required at some future time, a dental professional can easily remove the gutta-percha rubber because the gutta-percha rubber is naturally a rubber type material at the temperatures inside a human mouth.

Although gutta-percha rubber has several benefits as a material to fill and seal root canals, gutta-percha rubber also has several disadvantages. For example, the quality of the seal provided by gutta-percha rubber at the root end is highly dependent on how fast the molten gutta-percha rubber is delivered into the root canal prior to cooling. If the delivery process is too slow, the gutta-percha rubber begins to thicken before filling all the tiny spaces and holes within the root canal, which may leave unsealed gaps causing the seal to fail.

In an effort to minimize the disadvantages of gutta-percha rubber, root end sealers have been introduced to the dental industry. Conventional root end sealers deliver a superior seal over conventional gutta-percha because root end sealers are designed to flow into the tiny spaces and irregular gaps that are often difficult to fill with gutta-percha rubber. Moreover, conventional root end sealers are chemically cured (as opposed to gutta-percha rubber that simply hardens upon cooling), which allows the root end sealer time to penetrate all the tiny spaces at the root end and within the root canal before the root end sealer material begins to cure.

Although conventional root end sealers may provide a better seal compared to gutta-percha, conventional root end sealers also have several disadvantages. For example, one disadvantage with conventional root end sealers is the need for the dental professional to continue to use gutta-percha as an additional step after the root end sealer placement. In particular, conventional root end sealers typically cure into a hardened composite, which is much more difficult to remove than gutta-percha. Therefore, because dental professionals prefer the root end to be re-treatable after a root canal, dental professionals add a gutta-percha cone around the root-end sealer to allow future access to the root canal.

Additionally, conventional root end sealers have the disadvantage of requiring the dental professional to mix two compositions together just prior to delivery into the root canal. For example, conventional root end sealers may require the dental professional to mix two pastes together. This process takes valuable time, which of course makes the root canal procedure more expensive. Moreover, if the dental professional doesn't mix the two pastes properly, then the root sealer will not cure properly and the seal will likely fail.

Another disadvantage of conventional root end sealers is that the composition of conventional root end sealers may be limited to the chemical compatibility with various active ingredients that would be beneficial to include in the root end sealer. For example, conventional root end sealers may not be chemically compatible with active ingredients, such as calcium hydroxide, which is a popular anti-microbial agent used in dentistry. The main reason for the incompatibility is because calcium hydroxide is renowned for the deactivation of chemical cured cements used in conventional root end sealers.

Accordingly, there are a number of disadvantages in the conventional art of obturation materials.

SUMMARY OF THE INVENTION

Example embodiments of the present invention include compositions, materials, and methods that provide a single component tooth root sealer. The single component tooth root sealer can be designed to moisture cure at temperatures found within the human mouth. Examples of the single component tooth root sealer can include silicone compositions, such as condensation silicones of the alkoxy, acetoxy, and oxime type. Further examples of the single component tooth root sealer can include UV/visible light-initiators, antimicrobial agents, and radio-opaque compounds.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific example embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Figure 1:
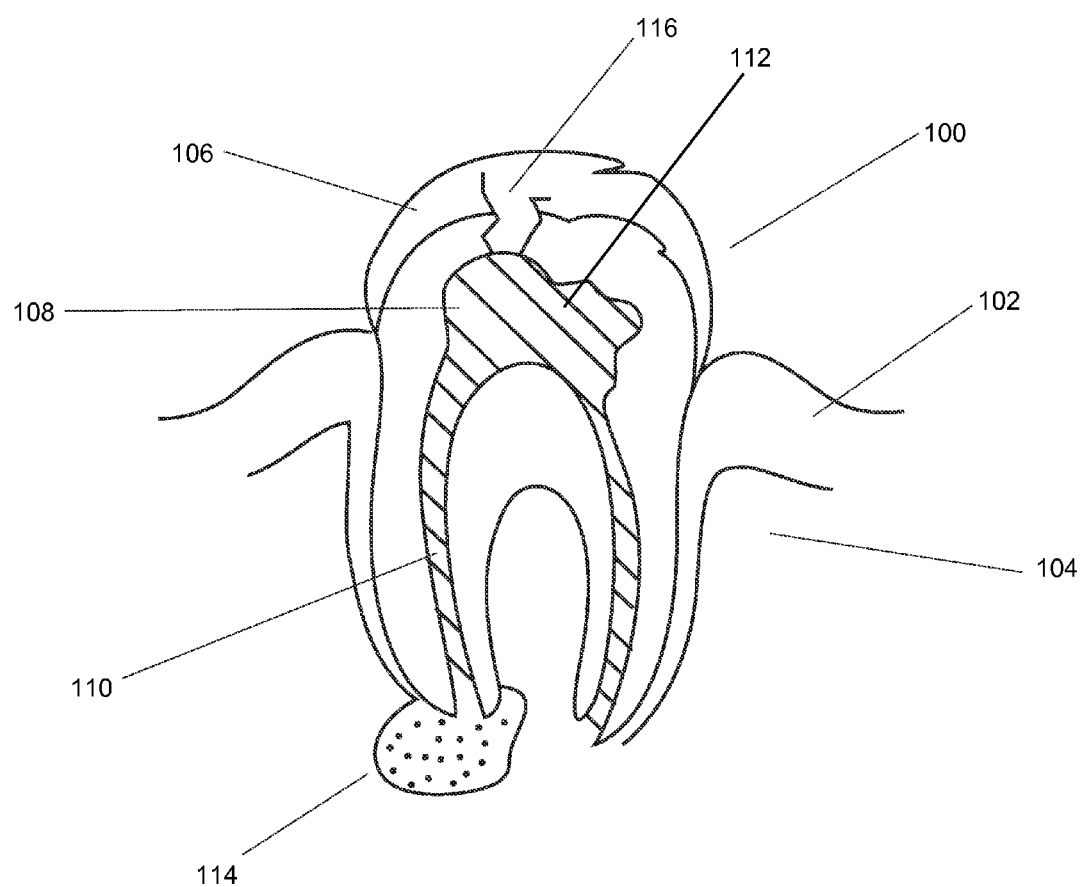
FIG. 1 illustrates a cross-sectional view of an unhealthy and infected tooth.

Example embodiments of the present invention include compositions, materials, and methods that provide a single component tooth root sealer. The single component tooth root sealer can be designed to moisture cure at temperatures found within the human mouth. Examples of the single component tooth root sealer can include silicone compositions, such as condensation silicones of the alkoxy, acetoxy, and oxime type. Further examples of the single component tooth root sealer can include UV/visible light-initiators, antimicrobial agents, and radio-opaque compounds.

As will be appreciated more fully herein, example embodiments of the present invention provide a single component tooth root sealer that does not require mixing or combining of any materials prior to using the single component tooth root sealer. For purposes of this application, the term "single component" means a chemical material and/or composition that can be stored in a ready-to-use, and therefore does not require any mixing, combining, or reaction with another chemical material or composition prior to the intended use.

Therefore, the single component tooth root sealer provides a more convenient tool for the dental professional compared to conventional tooth root sealers because the dental professional does not have to mix the material prior to use. In particular, example embodiments of the invention allow a dental professional to simply attach a delivery tip to a pre-filled delivery device containing the single component tooth root sealer and directly express the single component tooth root sealer into the root canal. In one example embodiment, the delivery device can be a syringe or similar device.

In addition to the added convenience of the single component tooth root sealer, example embodiments of the single component tooth root sealer, when cured, form silicone elastomers that have a permanent rubber like consistency. Therefore, the cured material easily allows the tooth to be re-treatable because a dental professional can easily remove the rubber like material from the tooth. In other words, when cured, the single component tooth root sealer exhibits the necessary characteristics that allow the dental professional to only need to use the single component tooth root sealer for purposes of sealing a root canal. This is superior to conventional tooth root sealers, which typically require that the dental professional perform an additional step of filling the root canal with gutta-percha after placing the conventional tooth root sealer.

Moreover, Applicant's experiments have shown that example embodiments of the single component root sealer disclosed in this application are chemically compatible with many useful active ingredients. For instance, example embodiments of the single component root sealer are compatible with calcium hydroxide. The addition of calcium hydroxide as an active ingredient provides a single component tooth root sealer that not only effectively seals the tooth root, but also delivers an antimicrobial agent that aids in disinfecting any residual necrotic tissue that remains in the pulp chamber after the root canal procedure. In essence, the addition of calcium hydroxide to the single component root sealer allows for the permanent existence of an antimicrobial ingredient within the pulp chamber long after the completion of the root canal procedure.

In addition, example embodiments of the single component tooth root sealer can also include radio-opaque compounds such that the single component tooth root sealer, once placed into a tooth, can easily be seen by X-ray imaging devices. Example radio-opaque compounds include, but are not limited to, the various salts and oxides of barium, strontium, bismuth, lead, zinc, calcium, yttrium, and gold. The radio-opaque compounds can be incorporated into the single component tooth root sealer by blending or mixing a fine powder of the chosen radio-opaque compound directly into the single component tooth root sealer so that a fine dispersion is achieved.

As briefly discussed above, the single component tooth root sealer can comprise a silicone composition of the alkoxy, oxime, or acetoxy types. Although each of these types of silicone can be used for various embodiments of the present invention, the silicone compositions based on the alkoxy and oxime types tended to produce more favorable results. Although fully functional single component tooth root sealer compositions are possible with oxime and acetoxy silicone compositions, for example purposes, the alkoxy based silicone composition will be used to describe one embodiment of the single component tooth root sealer in greater detail.

For example, one embodiment of the alkoxy based silicone composition can comprise the following: a polyalkoxysilane endcapped dimethyl silicone polymer; reinforcing fumed silica fillers; polydimethylsiloxane (PDMS) plasticizers; an alkoxy silane crosslinker; and/or a catalyst usually comprising a titanium alkoxide, tin salt, and moisture (any catalyst capable of catalyzing the polymerization of the polymer through moisture and/or heat may be used). In some examples of alkoxy based silicone compositions, the sole polymerization catalyst is moisture. Other similar alkoxy silicone based compositions can also be used.

The above described alkoxy based silicone composition produces little to no problematic reaction by-products. In particular, experimentation has shown that the alkoxy silicone composition releases about 1% methanol as a by-product, which is an insignificant amount of a relatively harmless substance to the root canal. In addition, the alkoxy based silicone compositions have an effective cure time that allows a period of time for the single component tooth root sealer to penetrate the root end and root canal effectively.

In another example embodiment of the single component tooth root sealer, LOCTITE NUVA-SIL 5248 ("Loctite") from Henkel Technologies, Inc. is used. Loctite 5248 is a moisture/UV light cured alkoxy silicone composition. As with other alkoxy based silicon compositions, Loctite is an ideal silicone composition for the stated purpose because Loctite has a low production of reaction by-products while curing. For example, Loctite typically produces about 0.1% to about 0.9% methyl alcohol as a by-product during a moisture cure. Moreover, Loctite is compatible with calcium hydroxide in concentrations of about 10% or above.

In addition, Loctite is curable by UV/visible light, which provides yet an additional option for the dental professional to ensure that the minimum cure state threshold has been achieved. The light cure absorption range of Loctite can be expanded by the addition of visible light photo-initiators like camphorquinone and IRGACURE 2022. The addition of visible light photo-initiators allows the silicone composition to cure by conventional curing lights already found in most dental offices.

Example embodiments of the single component tooth root sealer will now be demonstrated with reference to the following examples.

EXAMPLE 1

Irgacure 2022—0.5%
Calcium hydroxide—5.0%
Loctite 5248—84.5%
Barium Sulfate—10.0%

The composition described in Example 1 may be manufactured by blending the ingredients in a vacuum capable paddle mixer in a dehydrated environment, with the mixer equipment being dehydrated with acetone prior to use. The resulting single component tooth root sealer was tested for moisture cure in air at room temperature. The single component tooth root sealer went from a paste form to an elastomeric solid in about 24 to 48 hours after exposure to the air.

The resulting single component tooth root sealer was also tested for light cure capabilities and was found to surface cure to a depth of about 2 mm after exposure to 60 seconds of light with a dental light having an output of about 800 mw/cm2. The low surface skin thickness is due to the opaque calcium hydroxide blocking incoming light.

EXAMPLE 2

Irgacure 2022—1.0%
Calcium hydroxide—10.0%
Loctite 5248—79.0%
Bismuth oxy chloride—10.0%

The composition described in Example 2 may be manufactured by blending the ingredients in a vacuum capable paddle mixer in a dehydrated environment, with the mixer equipment being dehydrated with acetone prior to use. The resulting single component tooth root sealer was tested for moisture cure in air at room temperature. The single component tooth root sealer went from a paste form to an elastomeric solid in about 24 to 48 hours after exposure to the air.

The resulting single component tooth root sealer was also tested for light cure capabilities and was found to surface cure to a depth of about 2 mm after exposure to 60 seconds of light with a dental light having an output of about 800 mw/cm2. The low surface skin thickness is due to the opaque calcium hydroxide blocking incoming light.

The foregoing processes can be used to make similar effective compositions for a single component tooth root sealer using components and ranges selected from the following table.

| Material Component | Function | Compositional % Range |
| --- | --- | --- |
| Loctite 5248 | Alkoxy silicone composition | 1%-100% 10%-95% 50%-90% |
| Calcium Hydroxide | Anti-microbial | 0.1%-25% 2%-15% 5%-10% |
| Barium oxychloride | Radio-opaque compound | 1%-40% 3%-30% 8%-20% |
| Irgacure 2022/ Camphorquinone | Photo-initiators | 0.05%-5% 0.1%-3% 0.5%-1.5% |

Further example embodiments of single component tooth root sealers can utilize heat cured silicone compositions such that they remain un-polymerized at room temperatures and yet are capable of polymerization at elevated temperatures, especially if the polymerization temperature is that of the human body or about 37 Celsius. Heat cured compositions of the present invention are designed to be delivered by a delivery device into the root end and cured by means of the temperature difference found and produced in the human body. In order to ensure that the heat cured composition does not cure before being placed in the root canal, heat cured compositions may need refrigeration of the composition in order to preserve the shelf stability.

Once any of the above described compositions are prepared, the single component tooth root sealer may be loaded into a delivery device that is sealed and/or capped until used by a dental professional. In one example, the delivery device is a syringe. For example, in order to use the single component tooth root sealer, a dental professional removes the cap on the syringe, attaches an endodontic tip, inserts the endodontic tip in the root canal, and expresses the single component tooth root sealer to fill the root end and root canal. This method will be discussed in more detail with reference to FIGS. 1-4.

In particular, FIG. 1 illustrates an unhealthy or infected tooth 100. The tooth 100 is surrounded by gums 102 and a jaw bone 104. The tooth 100 includes an enamel and dentin portion 106, which is the hard structure of the tooth 100. The enamel and dentin portion 106 surrounds the pulp chamber 108 and the root canals 110. FIG. 1 illustrates that pulp material 112 is infected, and as is typically the case, the infection can extend not only throughout the root canal 110 and pulp chamber 108, but also into an infected region 114 located beyond the apex of the root. The infection can result from a host of various circumstances, including, for example, a crack 116 located in the enamel and dentin portion that permits bacteria to access the pulp chamber 108 and/or root canal 110.

Figure 2:
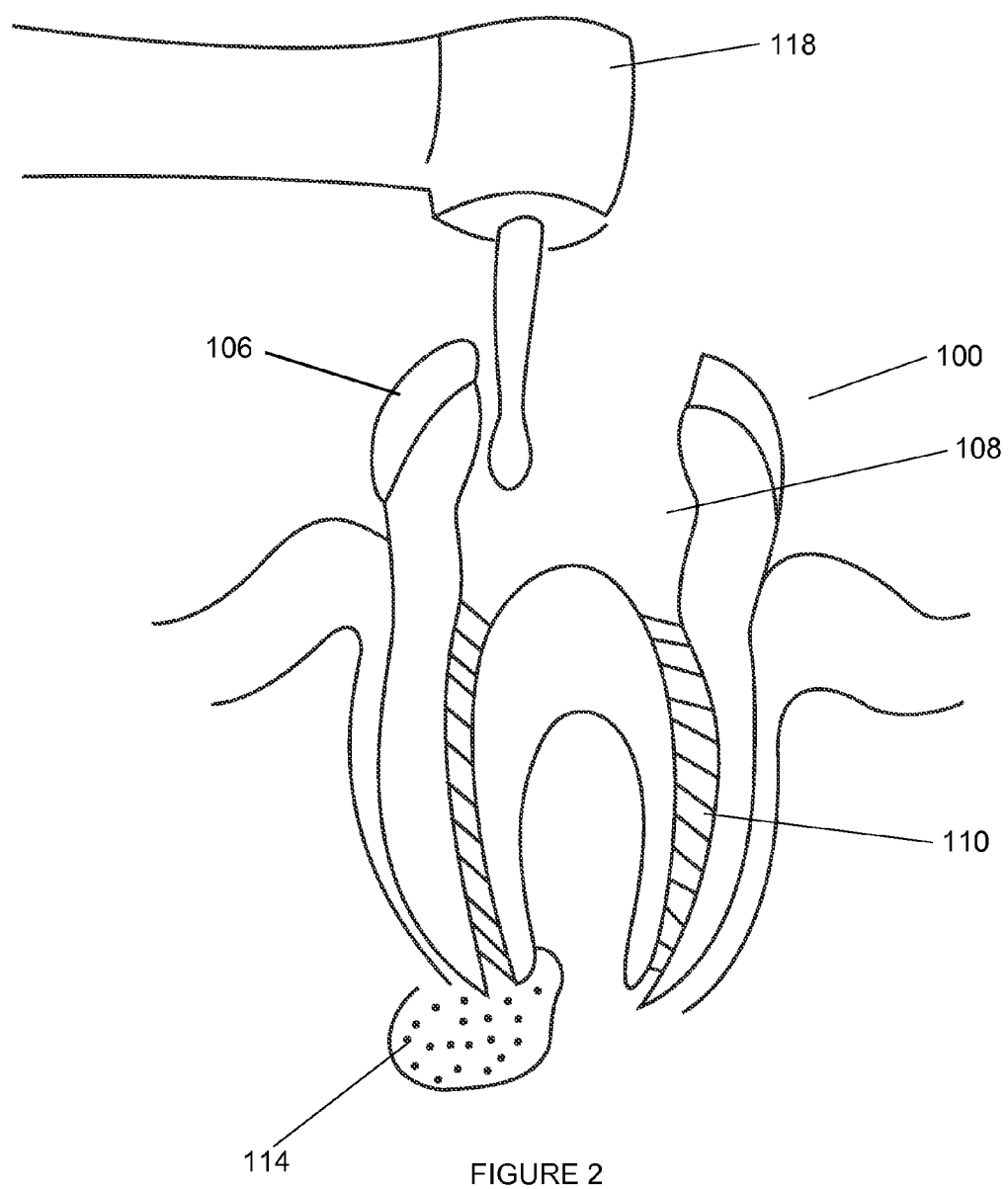
FIG. 2 illustrates a drill being used to remove the enamel and dentin from the tooth illustrated in FIG. 1.

Referring now to FIG. 2, a dental professional can use a drill 118 to remove at least a portion of the enamel and dentin portion 106 in order to gain access to the pulp chamber 108.

Figure 3:
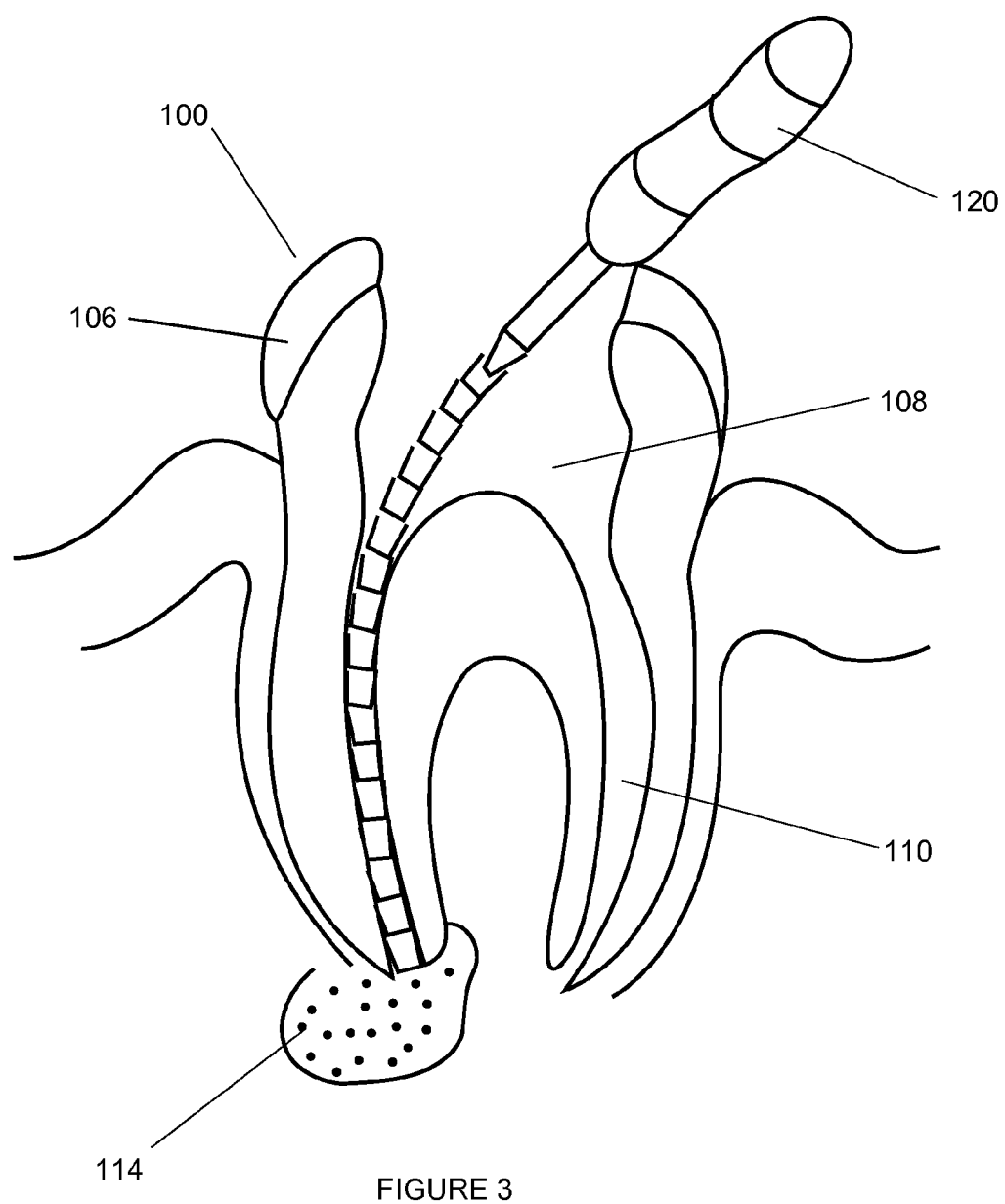
FIG. 3 illustrates an endodontic file being used to remove necrotic or infected tissue from the tooth illustrated in FIG. 1.

Once the dental profession has gained access to the pulp chamber 108, the dental professional can then use an endodontic file to remove and clean the necrotic pulp from the pulp chamber 108 and root canals 110, as illustrated in FIG. 3. Once the pulp chamber 108, root canals 110 and any other infected regions are cleaned of necrotic or otherwise infected tissue, the pulp chamber 108 and root canals 110 are irrigated with antibacterial fluids in preparation for filling and sealing the root canal.

Figure 4:
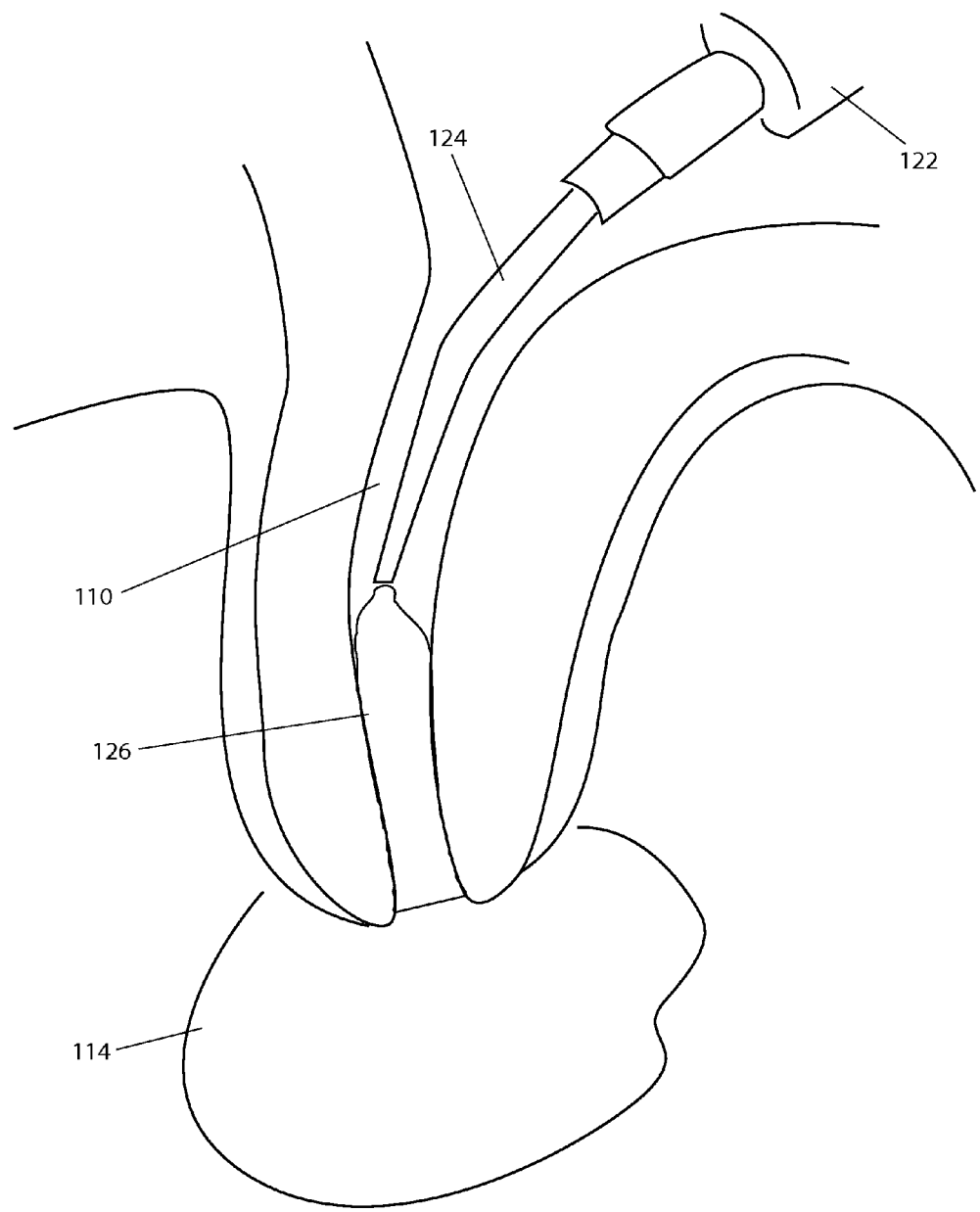
FIG. 4 illustrates a delivery device being used to expel a single component root end sealer into the root canal of the tooth illustrated in FIG. 1.

After the infected areas are cleaned, the dental professional is ready to fill the root canals with the single component tooth root sealer 126 that is described above. In particular, FIG. 4 illustrates that the dental professional obtains a delivery device 122 that contains the single component tooth root sealer 126. The dental professional can remove a cap (not shown) from the delivery device 122 and install an endodontic tip 124. The endodontic tip 124 can then be inserted into the root canal 110 and the dental professional can begin to express the single component tooth root sealer 126 into the root canal 110.

As further illustrated in FIG. 4, the dental professional can express the single component tooth root sealer 126 starting at the apex of the root, and filling the root canal 110 from the bottom up towards the pulp chamber. The dental professional may then proceed to fill the root canal located on the opposite side, and also fill as much as the pulp chamber as desired.

Following the expression of the single component tooth root sealer 126 into the root canal 110, the moisture located within the human mouth interacts with the single component tooth root sealer 126, causing the single component tooth root sealer to cure. In the embodiments of the single component tooth root sealer 126 that include photo-initiators, the dental professional can further the curing process by exposing the single component tooth root sealer to light generated from a conventional curing light found in most dentist offices. In other example methods, the dentist can use the curing light at various stages of the process of filling the root canal 110 with the single component tooth root sealer 126.

Portions of the single component tooth root sealer not exposed to direct moisture and/or UV/visible light (e.g., the portions of the single component tooth root sealer that is located away from a surface of the tooth root sealer) will continue to moisture cure and eventually fully cure about 24-48 hours later. However, the surface cure provided by the UV/visible light cure allows a dental professional to complete the dental procedure almost immediately following the UV/visible light cure.

Because the single component tooth root sealer can also include antimicrobial active ingredients as discussed above, it is possible for a dental professional to perform the above method of the root canal in a single visit, rather than having to schedule another appointment to ensure that all the infection is eliminated before sealing the root canal.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of sealing a tooth root after performing a root canal, comprising:
    obtaining a delivery device containing a single component tooth root sealer that is moisture curable, light curable, and in a ready-to-use state, the single component tooth root sealer comprising:
        between 50% and 90% alkoxy silicone composition;
        between 5%-10% anti-microbial agent;
        between 8%-20% radio-opaque compound; and
        between 0.5%-1.5% photo-initiator;
    expressing the single component tooth root sealer into the root canal; and
    exposing the expressed single component tooth root sealer to a visible light source and thereby light curing at least a portion of the expressed single component tooth root sealer.

2. The method recited in claim 1, further comprising:
    allowing the single component tooth root sealer to moisture cure within the root canal.

3. The method recited in claim 1, wherein the radio-opaque compound comprises barium oxychloride.

4. The method recited in claim 1, wherein the anti-microbial agent comprises calcium hydroxide.

* * * * *